US009012348B2

(12) United States Patent
Cheung et al.

(10) Patent No.: US 9,012,348 B2
(45) Date of Patent: Apr. 21, 2015

(54) SELECTIVE HYDROGENATION CATALYST AND METHODS OF MAKING AND USING SAME (71) Applicant: Chevron Phillips Chemical Company LP, The Woodlands, TX (US)

(72) Inventors: Tin-Tack Peter Cheung, Kingwood, TX (US); Zongxuan Hong, Houston, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 14/134,282

(22) Filed: Dec. 19, 2013

(65) Prior Publication Data

US 2014/0107383 A1    Apr. 17, 2014

Related U.S. Application Data (62) Division of application No. 12/710,781, filed on Feb. 23, 2010, now Pat. No. 8,633,127.

(60) Provisional application No. 61/157,491, filed on Mar. 4, 2009.

(51) Int. Cl.
*B01J 31/00* (2006.01)
*B01J 21/00* (2006.01)
(Continued)

(52) U.S. Cl.
CPC .............. *B01J 31/0271* (2013.01); *B01J 23/44* (2013.01); *B01J 23/66* (2013.01); *B01J 27/13* (2013.01);
(Continued)

(58) Field of Classification Search
USPC ......... 502/162, 262, 327, 328, 330, 333, 339, 502/439, 164
See application file for complete search history.

(56) References Cited

U.S. PATENT DOCUMENTS 3,463,830 A    8/1969  Dunning et al.
3,625,755 A   12/1971  Potrafke
(Continued)

FOREIGN PATENT DOCUMENTS

CN    1422695 A    6/2003
CN    1425637 A    6/2003
(Continued)

OTHER PUBLICATIONS

Boitiaux, J.P., et al., "Hydrogenation of highly unsaturated hydrocarbons over highly dispersed Pd catalyst. Part II: Ligand effect of piperidine," Applied Catalysis, 1985, vol. 15, pgs. 317-326, Elsevier Science Publishers B.V., Amsterdam, XP002577931.
Database, WPI, Week 200365, Thompson Scientific, London, GB, 2003-680539, CN1425637A, Jun. 25, 2003, 1 page, XP002577876.
Filing receipt and specification for provisional patent entitled "Selective hydrogenation catalyst and methods of making and using same," by Tin-Tack Peter Cheung, et al., filed Mar. 4, 2009 as U.S. Appl. No. 61/157,491.
(Continued)

*Primary Examiner* — Cam N. Nguyen
(74) *Attorney, Agent, or Firm* — Conley Rose, P.C.; Rodney B. Carroll; Monte R. Rhodes (57) ABSTRACT A composition comprising a supported hydrogenation catalyst comprising palladium and an organophosphorous compound, the supported hydrogenation catalyst being capable of selectively hydrogenating highly unsaturated hydrocarbons to unsaturated hydrocarbons. A method of making a selective hydrogenation catalyst comprising contacting a support with a palladium-containing compound to form a palladium supported composition, contacting the palladium supported composition with an organophosphorus compound to form a catalyst precursor, and reducing the catalyst precursor to form the catalyst. A method of selectively hydrogenating highly unsaturated hydrocarbons to an unsaturated hydrocarbon enriched composition comprising contacting a supported catalyst comprising palladium and an organophosphorous compound with a feed comprising highly unsaturated hydrocarbon under conditions suitable for hydrogenating at least a portion of the highly unsaturated hydrocarbon feed to form the unsaturated hydrocarbon enriched composition.

15 Claims, 2 Drawing Sheets (51) Int. Cl.

| | | |
|---|---|---|
| *B01J 21/04* | (2006.01) | |
| *B01J 23/00* | (2006.01) | |
| *B01J 23/02* | (2006.01) | |
| *B01J 23/40* | (2006.01) | |
| *B01J 23/42* | (2006.01) | |
| *B01J 23/44* | (2006.01) | |
| *B01J 23/58* | (2006.01) | |
| *B01J 31/02* | (2006.01) | |
| *B01J 23/66* | (2006.01) | |
| *B01J 27/13* | (2006.01) | |
| *B01J 31/16* | (2006.01) | |
| *B01J 31/18* | (2006.01) | |
| *B01J 31/24* | (2006.01) | |
| *B01J 37/02* | (2006.01) | |
| *B01J 37/28* | (2006.01) | |
| *C10G 45/40* | (2006.01) | |
| *C07C 5/09* | (2006.01) | |
| *B01J 35/00* | (2006.01) | |
| *B01J 35/02* | (2006.01) | |
| *B01J 35/10* | (2006.01) | |

(52) U.S. Cl.
CPC .......... *B01J 31/1616* (2013.01); *B01J 31/1845* (2013.01); *B01J 31/185* (2013.01); *B01J 31/1865* (2013.01); *B01J 31/1875* (2013.01); *B01J 31/24* (2013.01); *B01J 31/2404* (2013.01); *B01J 35/008* (2013.01); *B01J 35/023* (2013.01); *B01J 35/1009* (2013.01); *B01J 35/1014* (2013.01); *B01J 37/0203* (2013.01); *B01J 37/024* (2013.01); *B01J 37/28* (2013.01); *B01J 2231/645* (2013.01); *B01J 2531/824* (2013.01); *C10G 45/40* (2013.01); *C10G 2300/703* (2013.01); *C07C 5/09* (2013.01)

(56) References Cited

U.S. PATENT DOCUMENTS

| | | | |
|---|---|---|---|
| 3,635,841 | A | 1/1972 | Keith et al. |
| 3,947,495 | A * | 3/1976 | Murib et al. ................... 502/168 |
| 4,120,901 | A | 10/1978 | Hobbs et al. |
| 4,204,997 | A | 5/1980 | Hobbs et al. |
| 4,325,834 | A | 4/1982 | Bartish et al. |
| 4,384,981 | A | 5/1983 | Dines et al. |
| 4,404,124 | A | 9/1983 | Johnson et al. |
| 4,484,015 | A | 11/1984 | Johnson et al. |
| 4,713,363 | A | 12/1987 | Hucul |
| 4,774,221 | A | 9/1988 | Medem et al. |
| 4,786,623 | A * | 11/1988 | Grenouillet et al. .......... 502/164 |
| 4,889,949 | A * | 12/1989 | Grenouillet et al. .......... 560/202 |
| 5,028,576 | A | 7/1991 | Drent et al. |
| 5,113,022 | A | 5/1992 | Abatjoglou et al. |
| 5,166,116 | A | 11/1992 | Drent et al. |
| 5,189,003 | A | 2/1993 | Klusener et al. |
| 5,482,596 | A | 1/1996 | Wu |
| 5,712,403 | A | 1/1998 | Sato et al. |
| 5,880,301 | A | 3/1999 | Shibasaki et al. |
| 6,005,123 | A | 12/1999 | Dessau et al. |
| 6,140,265 | A | 10/2000 | Haber et al. |
| 6,197,716 | B1 | 3/2001 | Baumeister et al. |
| 6,197,720 | B1 * | 3/2001 | Heineke et al. ............... 502/325 |
| 6,232,262 | B1 | 5/2001 | Sielcken et al. |
| 6,541,417 | B2 | 4/2003 | Kasztelan et al. |
| 6,603,038 | B1 * | 8/2003 | Hagemeyer et al. ......... 560/241.1 |
| 6,635,600 | B1 * | 10/2003 | Kimble et al. ................ 502/330 |
| 6,717,016 | B2 | 4/2004 | Shimizu et al. |
| 6,794,328 | B2 | 9/2004 | Yokozawa et al. |
| 6,821,412 | B1 | 11/2004 | Fujukawa et al. |
| 6,831,035 | B2 | 12/2004 | Puckette et al. |
| 6,852,661 | B1 | 2/2005 | Ahlers et al. |
| 6,921,733 | B2 | 7/2005 | Mahajan |
| 6,969,694 | B2 | 11/2005 | Zhang |
| 6,987,202 | B2 | 1/2006 | Shimizu et al. |
| 7,148,176 | B2 | 12/2006 | Beller et al. |
| 7,160,835 | B2 | 1/2007 | Tsuji |
| 7,408,089 | B2 | 8/2008 | Ryu |
| 7,417,007 | B2 | 8/2008 | Cheung et al. |
| 7,586,010 | B2 | 9/2009 | Liu et al. |
| 7,704,912 | B2 | 4/2010 | Reetz et al. |
| 7,737,075 | B2 | 6/2010 | Ryu |
| 7,737,079 | B2 | 6/2010 | Ryu |
| 8,461,072 | B2 | 6/2013 | Zhao et al. |
| 8,633,127 | B2 | 1/2014 | Cheung et al. |
| 2004/0192983 | A1 | 9/2004 | Bergmeister et al. |
| 2004/0260126 | A1 | 12/2004 | Augustine et al. |
| 2007/0161833 | A1 | 7/2007 | Bergmeister, III et al. |

FOREIGN PATENT DOCUMENTS

| | | | |
|---|---|---|---|
| CN | 102341175 | A | 2/2012 |
| EP | 0933129 | A1 | 8/1999 |
| EP | 2403642 | A2 | 1/2012 |
| JP | 08066633 | A | 3/1996 |
| JP | 09000937 | A | 1/1997 |
| JP | 2007518676 | A | 7/2007 |
| WO | 0023403 | A1 | 4/2000 |
| WO | 2005000773 | A1 | 1/2005 |
| WO | 2010101736 | A2 | 9/2010 |
| WO | 2010101736 | A3 | 9/2010 |

OTHER PUBLICATIONS

Foreign communication from a related counterpart application—Chinese Office Action, Application No. 201080010107.4, Jan. 31, 2013, 7 pages.

Foreign communication from a related counterpart application—Chinese Office Action, Application No. 201080010107.4, Aug. 21, 2013, 8 pages.

Foreign communication from a related counterpart application—Chinese Office Action, Application No. 201080010107.4, Mar. 5, 2014, 10 pages.

Foreign communication from a related counterpart application—Invitation to Pay Additional Fees, PCT/US2010/025038, Jun. 14, 2010, 9 pages.

Foreign communication from a related counterpart application—International Search Report and Written Opinion, PCT/US2010/025038, Nov. 26, 2010, 18 pages.

Foreign communication from a related counterpart application—International Preliminary Report on Patentability, Sep. 6, 2011, PCT/US2010/025038, 10 pages.

Foreign communication from a related counterpart application—Japanese Office Action, Application No. 2011-552975, Aug. 16, 2013, 6 pages.

Kwon, Min Serk, et al., "Palladium nanoparticles entrapped in aluminum hydroxide: dual catalyst for alkene hydrogenation and aerobic alcohol oxidation," Organic Letters, 2005, vol. 7, No. 6, pp. 1077-1079, American Chemical Society, XP002577877.

Song, Choong Eui, et al., "Supported chiral catalysts on inorganic materials," Chem. Rev., 2002, vol. 102, No. 10, pp. 3495-3524, American Chemical Society, XP002297471.

UOP Method 578-02, "Automated Pore Volume and Pore Size Distribution of Porous Substances by Mercury Porosimetry," UOP LLC, 1984, pp. 1-14.

Westermark, Gunnar, et al., "An infrared study on the chemisorption of tertiary phosphines on coinage and platinum group metal surfaces," Colloids and Surfaces, A: Physicochemical and Engineering Aspects, 1999, vol. 150, pp. 31-43, Elsevier Science, B.V.

Westermark, Gunnar, et al., "Chemisorption of tertiary phosphines on coinage and platinum group metal powders. An infrared reflectance absorption spectroscopic, enhanced Raman spectroscopic and surface coverage study," Colloids and Surfaces, A: Physicochemical and Engineering Aspects, 1998, vol. 144, pp. 149-166, Elsevier Science B.V.

* cited by examiner

SELECTIVE HYDROGENATION CATALYST AND METHODS OF MAKING AND USING SAME

CROSS-REFERENCE TO RELATED APPLICATIONS

This application is a divisional of and claims priority to U.S. patent application Ser. No. 12/710,781 filed on Feb. 23, 2010, published as US 2010/0228065 A1, which claims priority to U.S. Provisional Patent Application Ser. No. 61/157,491, filed Mar. 4, 2009 and entitled "Selective Hydrogenation Catalyst and Methods of Making and Using Same," which is hereby incorporated herein by reference in its entirety for all purposes.

STATEMENT REGARDING FEDERALLY SPONSORED RESEARCH OR DEVELOPMENT

Not applicable.

REFERENCE TO A MICROFICHE APPENDIX

Not applicable.

BACKGROUND

1. Technical Field

The present disclosure relates to the production of unsaturated hydrocarbons, and more particularly to a selective hydrogenation catalyst and methods of making and using same.

2. Background

Unsaturated hydrocarbons such as ethylene and propylene are often employed as feedstocks in preparing value added chemicals and polymers. Unsaturated hydrocarbons may be produced by pyrolysis or steam cracking of hydrocarbons including hydrocarbons derived from coal, hydrocarbons derived from synthetic crude, naphthas, refinery gases, ethane, propane, butane, and the like. Unsaturated hydrocarbons produced in these manners usually contain small proportions of highly unsaturated hydrocarbons such as acetylenes and diolefins that adversely affect the production of subsequent chemicals and polymers. Thus, to form an unsaturated hydrocarbon product such as a polymer grade monoolefin, the amount of acetylenes and diolefins in the monoolefin stream is typically reduced. For example, in polymer grade ethylene, the acetylene content typically is less than about 2 ppm.

One technique commonly used to reduce the amount of acetylenes and diolefins in an unsaturated hydrocarbon stream primarily comprising monoolefins involves selectively hydrogenating the acetylenes and diolefins to monoolefins. This process is selective in that hydrogenation of the monoolefin and the highly unsaturated hydrocarbons to saturated hydrocarbons is minimized. For example, the hydrogenation of ethylene or acetylene to ethane is minimized.

One challenge to the selective hydrogenation process is the potential for runaway reactions that lead to the uncontrollable reduction of ethylene to ethane. One methodology to minimize runaway reactions is to increase the amount of selectivity enhancers in the hydrogenation catalyst. Thus, catalyst preparations may comprise one or more selectivity enhancers. Selectivity enhancers are materials such as alkali metal halides that increase the catalyst selectivity for the hydrogenation of highly unsaturated olefins to unsaturated olefins. The use of additional amounts of selectivity enhancers, also termed increased loadings, may lead to improved catalyst selectivity; however, the increased loadings may have drawbacks such as decreased catalyst activity. Therefore, a need exists for a hydrogenation catalyst that has a desired selectivity and activity.

SUMMARY

Disclosed herein is a composition comprising a supported hydrogenation catalyst comprising palladium and an organophosphorous compound, the supported hydrogenation catalyst being capable of selectively hydrogenating highly unsaturated hydrocarbons to unsaturated hydrocarbons.

Also disclosed herein is a method of making a selective hydrogenation catalyst comprising contacting a support with a palladium-containing compound to form a palladium supported composition, contacting the palladium supported composition with an organophosphorus compound to form a catalyst precursor, and reducing the catalyst precursor to form the catalyst.

Further disclosed herein is a method of selectively hydrogenating highly unsaturated hydrocarbons to an unsaturated hydrocarbon enriched composition comprising contacting a supported catalyst comprising palladium and an organophosphorous compound with a feed comprising highly unsaturated hydrocarbon under conditions suitable for hydrogenating at least a portion of the highly unsaturated hydrocarbon feed to form the unsaturated hydrocarbon enriched composition.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

In an embodiment, a method of making a selective hydrogenation catalyst comprises contacting an inorganic catalyst support with a palladium-containing compound to form a palladium supported composition and contacting the palladium supported composition with an organophosphorus compound. Herein, the disclosure will focus on the use of phosphine oxides, phosphates, phosphinates, and phosphonates as the organophosphorus compound, although phosphines phosphites, phosphinites, and phosphonites are also contemplated organophosphorus compound precursors and will be described in more detail later herein. In an embodiment, the organophosphorus compound functions to increase the selectivity of the hydrogenation catalyst for the conversion of a highly unsaturated hydrocarbon to an unsaturated hydrocarbon. Herein, such catalysts are termed palladium, organophosphorus supported catalysts (PPSC).

The PPSC may be used for selectively hydrogenating highly unsaturated hydrocarbons to unsaturated hydrocarbons. As used herein, a highly unsaturated hydrocarbon is defined as a hydrocarbon containing a triple bond, two conjugated carbon-carbon double bonds, or two cumulative carbon-carbon double bonds. As used herein, an unsaturated hydrocarbon is defined as a hydrocarbon containing an isolated carbon-carbon double bond. Examples of highly unsaturated hydrocarbons include without limitation acetylene, methylacetylene, and propadiene. Examples of unsaturated hydrocarbons include ethylene and propylene. It is also understood that the term "catalyst" refers to the support together with the materials impregnated in or on the support.

In an embodiment, the PPSC may comprise an inorganic support such as for example and without limitation aluminas, silicas, titanias, zirconias, aluminosilicates (e.g., clays, ceramics, and/or zeolites), spinels (e.g., zinc aluminate, zinc titanate, and/or magnesium aluminate), or combinations thereof. In an embodiment, the PPSC comprises an alumina support. In some embodiments, the alumina support comprises an alpha ($\alpha$)-alumina support.

The inorganic support may have a surface area of from about 2 to about 100 square meters per gram ($m^2/g$), alternatively of from about 2 $m^2/g$ to about 75 $m^2/g$, alternatively of from about 3 $m^2/g$ to about 50 $m^2/g$, alternatively of from about 4 $m^2/g$ to about 25 $m^2/g$, alternatively of from about 5 $m^2/g$ to about 10 $m^2/g$. The surface area of the support may be determined using any suitable method. An example of a suitable method includes the Brunauer, Emmett, and Teller ("BET") method, which measures the quantity of nitrogen adsorbed on the support. Alternatively, the surface area of the support can be measured by a mercury intrusion method such as is described in ASTM UOP 578-02, entitled "Automated Pore Volume and Pore Size Distribution of Porous Substances by MERCURY Porosimetry," which is incorporated herein by reference in its entirety.

Particles of the inorganic support generally have an average diameter of from about 1 mm to about 10 mm, alternatively from about 2 mm to about 6 mm, alternatively from about 2 mm to about 4 mm, alternatively from about 4 mm to about 6 mm and can have any suitable shape. In an embodiment, the shape of the inorganic support may be cylindrical. In an alternative embodiment, the shape of the inorganic support may be spherical.

In an embodiment, the inorganic support may be present in an amount such that it comprises the balance of the PPSC when all other components are accounted for.

In an embodiment, the PPSC comprises palladium. The palladium may be added to the PPSC by contacting the inorganic support with a palladium-containing compound to form a palladium supported composition as will be described in more detail later herein. Examples of suitable palladium-containing compounds include without limitation palladium chloride, palladium nitrate, ammonium hexachloropalladate, ammonium tetrachlopalladate, palladium acetate, palladium bromide, palladium iodide, tetraamminepalladium nitrate, or combinations thereof. In an embodiment, the palladium-containing compound is a component of an aqueous solution. An example of palladium-containing solution suitable for use in this disclosure includes without limitation a solution comprising palladium metal.

In an embodiment, the PPSC may be prepared using a palladium-containing compound in an amount of from about 0.005 wt. % to about 5 wt. % based on the total weight of the PPSC, alternatively from about 0.01 wt. % to about 3 wt. %, alternatively from about 0.02 wt. % to about 1 wt. %, alternatively from about 0.02 wt. % to about 0.04 wt. %, alternatively from about 0.03 wt. % to about 0.05 wt. %. The amount of palladium incorporated into the PPSC may be in the range described herein for the amount of palladium-containing compound used to prepare the PPSC.

In an embodiment, the PPSC comprises an organophosphorus compound. In an embodiment, the organophosphorus compound can be represented by the general formula of $(R)_x(OR')_yP=O$; wherein x and y are integers ranging from 0 to 3 and x plus y equals 3; wherein each R may be hydrogen, a hydrocarbyl group, or combinations thereof; and wherein each R' may a hydrocarbyl group. In some embodiments, the organophosphorus compound may include compounds such as phosphine oxides, phosphinates, phosphonates, phosphates, or combinations of any of the foregoing. For purposes of this application, the term "hydrocarbyl(s)" or "hydrocarbyl group(s)" is used herein in accordance with the definition specified by IUPAC: as a univalent group or groups derived by the removal of one hydrogen atom from a carbon atom of a "hydrocarbon." A hydrocarbyl group can be an aliphatic, inclusive of acyclic and cyclic groups. A hydrocarbyl group can include rings, ring systems, aromatic rings, and aromatic ring systems. Hydrocarbyl groups may include, by way of example, aryl, alkyl, cycloalkyl, and combinations of these groups, among others. Hydrocarbyl groups may be linear or branched unless otherwise specified. For the purposes of this application, the terms "alkyl," or "cycloalkyl" refers to a univalent group derived by removal of a hydrogen atom from any carbon atom of an alkane. For the purposes of this application, the terms "aryl," or "arylene" refers to a univalent group derived by removal of a hydrogen atom from any carbon atom of an aryl ring.

In an embodiment, the hydrocarbyl group can have from 1 to 30 carbon atoms, alternatively from 2 to 20 carbon atoms, alternatively from 3 to 15 carbon atoms. In other embodiments, the hydrocarbyl group can have from about 6 to about 30 carbon atoms, alternatively from about 6 to about 20 carbon atoms, alternatively from about 6 to about 15 carbon atoms.

Generally, the alkyl group for any feature which calls for an alkyl group described herein can be a methyl, ethyl, n-propyl (1-propyl), isopropyl (2-propyl), n-butyl (1-butyl), sec-butyl (2-butyl), isobutyl (2-methyl-1-propyl), tert-butyl (2-methyl-2-propyl), n-pentyl (1-pentyl), 2-pentyl, 3-pentyl, 2-methyl-1-butyl, tert-pentyl (2-methyl-2-butyl), 3-methyl-1-butyl, 3-methyl-2-butyl, neo-pentyl (2,2-dimethyl-1-propyl), n-hexyl (1-hexyl) group. Persons having ordinary skill in the art with the aids of this disclosure will readily recognize which alkyl group represents primary, secondary, or tertiary alkyl groups.

Organophosphorus compounds described herein are not considered to encompass elemental phosphorus, or inorganic phosphorus compounds, except that which may be produced during the preparation of the PPSC described herein. Inorganic phosphorus compounds encompass monobasic, dibasic, and tribasic phosphates such as tribasic potassium phosphate ($K_3PO_4$), tribasic sodium phosphate ($Na_3PO_4$), dibasic potassium phosphate ($K_2HPO_4$), dibasic sodium phosphate ($Na_2HPO_4$), monobasic potassium phosphate ($KH_2PO_4$), monobasic sodium phosphate ($NaH_2PO_4$). Inorganic phosphorus compounds also encompass the corresponding phosphorus acid of above mentioned salts. Inorganic phosphorus compounds also encompass anionic inorganic phosphorus compounds containing pentavalent phosphorus, and halogens. Examples of anionic inorganic phosphorus compounds include sodium and potassium hexafluorophosphate.

An organophosphorus compound suitable for use in this disclosure may be further characterized by a low-boiling point wherein a low boiling point refers to a boiling point of about 100° C. Alternatively, an organophosphorus compound suitable for use in this disclosure may be further characterized by a high boiling point wherein a high boiling point refers to a boiling point of equal to or greater than about 300° C.

In an embodiment, the organophosphorus compound comprises a phosphine oxide which can be represented by the general formula of $(R)_3P=O$; wherein each R may be hydrogen, a hydrocarbyl group, or combinations thereof. Examples of phosphine oxides suitable for use in this disclosure include without limitation butyldiethylphosphine oxide, butyldimethylphosphine oxide, butyldiphenylphosphine oxide, butyldipropylphosphine oxide, decyldiethylphosphine oxide, decyldimethylphosphine oxide, decyldiphenylphosphine oxide, dibutyl(2-methylphenyl)-phosphine oxide, diethyl(3-methylphenyl)-phosphine oxide, ethyldioctylphosphine oxide, ethyldibutylphosphine oxide, ethyldimethylphosphine oxide, ethyldiphenylphosphine oxide, ethyldipropylphosphine oxide, heptyldibutylphosphine oxide, heptyldiethylphosphine oxide, heptyldimethyl phosphine oxide, heptyldipentylphosphine oxide, heptyldiphenylphosphine oxide, hexyldibutylphosphine oxide, hexyldiethylphosphine oxide, hexyldimethyl phosphine oxide, hexyldipentylphosphine oxide, hexyldiphenylphosphine oxide, methylbis(4-methylphenyl)-phosphine oxide, methyldibutylphosphine oxide, methyldidecylphosphine oxide, methyldiethylphosphine oxide, methyldiphenylphosphine oxide, methyldipropylphosphine oxide, octyldimethylphosphine oxide, octyldiphenylphosphine oxide, pentyldibutylphosphine oxide, pentyldiethylphosphine oxide, pentyldimethylphosphine oxide, pentyldiphenylphosphine oxide, phenyldibutylphosphine oxide, phenyldiethylphosphine oxide, phenyldimethylphosphine oxide, phenyldipropylphosphine oxide, propyldibutylphosphine oxide, propyldimethylphosphine oxide, propyldiphenylphosphine oxide, tris(2,6-dimethylphenyl)-phosphine oxide, tris(2-methylphenyl)-phosphine oxide, tris(4-methylphenyl)-phosphine oxide, tris[4-(1,1-dimethylethyl)phenyl]-phosphine oxide, (1-methylethyl)diphenylphosphine oxide, 4-(diphenylmethyl)phenyl]diphenylphosphine oxide, bis(2-methylphenyl)(2-methylpropyl)-phosphine oxide, or combinations thereof. In some embodiments, the phosphine oxides suitable for use in this disclosure include without limitation tributylphosphine oxide, triethylphosphine oxide, triheptylphosphine oxide, trimethylphosphine oxide, trioctylphosphine oxide, tripentylphosphine oxide, tripropylphosphine oxide, triphenylphosphine oxide, or combinations thereof.

In an embodiment, the organophosphorus compound comprises an organic phosphate which can be represented by the general formula of $(OR')_3P=O$; wherein each R' may a hydrocarbyl group. Examples of phosphates suitable for use in this disclosure include without limitation (1-methylethyl) diphenyl phosphate, 2-ethylphenyldiphenyl phosphate, 4-(diphenylmethyl)phenyl]diphenyl phosphate, bis(2-methylphenyl)(2-methylpropyl)phosphate, butyldiethylphosphate, butyldimethylphosphate, butyldiphenylphosphate, butyldipropylphosphate, crecyldiphenylphosphate, decyldiethylphosphate, decyldimethylphosphate, decyldiphenylphosphate, dibutyl(2-methylphenyl)phosphate, diethyl(3-methylphenyl)phosphate, ethyldibutylphosphate, ethyldimethylphosphate, ethyldioctylphosphate, ethyldiphenylphosphate, ethyldipropylphosphate, heptyldibutylphosphate, heptyldiethylphosphate, heptyldimethyl phosphate, heptyldipentylphosphate, heptyldiphenylphosphate, hexyldibutylphosphate, hexyldiethylphosphate, hexyldimethyl phosphate, hexyldipentylphosphate, hexyldiphenylphosphate, methylbis(4-methylphenyl)phosphate, methyldibutylphosphate, methyldidecylphosphate, methyldiethylphosphate, methyldiphenylphosphate, methyldipropylphosphate, octyldimethylphosphate, octyldiphenylphosphate, pentyldibutylphosphate, pentyldiethylphosphate, pentyldimethylphosphate, pentyldiphenylphosphate, phenyldibutylphosphate, phenyldiethylphosphate, phenyldimethylphosphate, phenyldipropylphosphate, propyldibutylphosphate, propyldimethylphosphate, propyldiphenylphosphate, tri(2,3-dichloropropyl)phosphate, tri(2,6-dimethylphenyl)phosphate, tri(2-chloroethyl)phosphate, tri(nonylphenyl) phosphate, tris(2,6-dimethylphenyl)phosphate, tris(2-methylphenyl)phosphate, tris(4-methylphenyl)phosphate, tris[4-(1,1-dimethylethyl)phenyl]phosphate, or combinations thereof. In some embodiments, the phosphates suitable for use in this disclosure include without limitation tributylphosphate, tricresyl phosphate, tricyclohexyl phosphate, tridecylphosphate, triethylphosphate, triheptylphosphate, triisopropyl phosphate, trimethylphosphate, trioctadecyl phosphate, trioctylphosphate, tripentylphosphate, triphenylphosphate, tripropylphosphate, trixylylphosphate, or combinations thereof.

In an embodiment, the organophosphorus compound comprises a phosphinate, which can be represented by the general formula of $(R)_2(OR')P=O$; wherein each R may be hydrogen, a hydrocarbyl group, or combinations thereof; and wherein each R' may a hydrocarbyl group. Examples of phosphinates suitable for use in this disclosure include without limitation butyl butylphosphinate, butyl dibutylphosphinate, butyl diethylphosphinate, butyl diphenylphosphinate, butyl dipropylphosphinate, butyl ethylphosphinate, butyl heptylphosphinate, butyl hexylphosphinate, butyl pentylphosphinate, butyl phenylphosphinate, butyl propylphosphinate, decyl pentylphosphinate, butyl butylpentylphosphinate, ethyl butylphosphinate, ethyl decylphosphinate, ethyl dibutylphosphinate, ethyl diethylphosphinate, ethyl dimethylphosphinate, ethyl diphenylphosphinate, ethyl dipropylphosphinate, ethyl ethylphosphinate, ethyl heptylphosphinate, ethyl hexylphosphinate, ethyl octylphosphinate, ethyl pentylphosphinate, ethyl phenylphosphinate, ethyl propylphosphinate, heptyl dibutylphosphinates, heptyl pentylphosphinate, heptylphosphinate, hexyl dibutylphosphinate, hexyl pentylphosphinate, isopropyl diphenylphosphinate, methyl butylphosphinate, methyl decylphosphinate, methyl dibutylphosphinate, methyl diethylphosphinate, methyl dimethylphosphinate, methyl diphenylphosphinates, methyl dipropylphosphinate, methyl ethylphosphinate, methyl heptylphosphinate, methyl hexylphosphinate, methyl octylphosphinate, methyl pentylphosphinate, methyl phenylphosphinate, methyl propylphosphinate, octyl pentylphosphinate, octylphosphinate, pentyl dibutylphosphinate, pentylphosphinate, phenyl butylphosphinate, phenyl decylphosphinate, phenyl dibutylphosphinate, phenyl diethylphosphinate, phenyl diethylphosphinate, phenyl dimethylphosphinate, phenyl diphenylphosphinate, phenyl diphenylphosphinate, phenyl dipropylphosphinate, phenyl ethylphosphinate, phenyl heptylphosphinate, phenyl hexylphosphinate, phenyl octylphosphinate, phenyl pentylphosphinate, phenyl pentylphosphinate, phenyl phenylphosphinate, phenyl propylphosphinate, phenylphosphinate, propyl diphenylphosphinate, or combinations thereof.

In an embodiment, the organophosphorus compound comprises a phosphonate, which can be represented by the general formula of $(R)(OR')_2P=O$; wherein each R may be hydrogen, a hydrocarbyl group, or combinations thereof; and wherein each R' may a hydrocarbyl group. Examples of phosphonates suitable for use in this disclosure include without limitation (1-methylethyl)diphenyl phosphonate, 2-ethylphenyldiphenyl phosphonate, 4-(diphenylmethyl)phenyl]diphenyl phosphonate, bis(2-methylphenyl)(2-methylpropyl)phosphonate, butyldiethylphosphonate, butyldimethylphosphonate, butyldiphenylphosphonate, butyldipropylphosphonate, crecyldiphenylphosphonate, decyldiethylphosphonate, decyldimethylphosphonate, decyldiphenylphosphonate, dibutyl(2-methylphenyl)phosphonate, diethyl(3-methylphenyl)phosphonate, ethyldibutylphosphonate, ethyldimethylphosphonate, ethyldioctylphosphonate, ethyldiphenylphosphonate, ethyldipropylphosphonate, heptyldibutylphosphonate, heptyldiethylphosphonate, heptyldimethyl phosphonate, heptyldipentylphosphonate, heptyldiphenylphosphonate, hexyldibutylphosphonate, hexyldiethylphosphonate, hexyldimethyl phosphonate, hexyldipentylphosphonate, hexyldiphenylphosphonate, methylbis(4-methylphenyl)phosphonate, methyldibutylphosphonate, methyldidecylphosphonate, methyldiethylphosphonate, methyldiphenylphosphonate, methyldipropylphosphonate, octyldimethylphosphonate, octyldiphenylphosphonate, pentyldibutylphosphonate, pentyldiethylphosphonate, pentyldimethylphosphonate, pentyldiphenylphosphonate, phenyldibutylphosphonate, phenyldiethylphosphonate, phenyldimethylphosphonate, phenyldipropylphosphonate, propyldibutylphosphonate, propyldimethylphosphonate, propyldiphenylphosphonate, tri(2,3-dichloropropyl)phosphonate, tri(2,6-dimethylphenyl)phosphonate, tri(2-chloroethyl)phosphonate, tri(nonylphenyl)phosphonate, tris(2,6-dimethylphenyl)phosphonate, tris(2-methylphenyl)phosphonate, tris(4-methylphenyl)phosphonate, tris[4-(1,1-dimethylethyl)phenyl]phosphonate, or combinations thereof. In some embodiments, the phosphonates suitable for use in this disclosure include without limitation tributylphosphonate, tricresyl phosphonate, tricyclohexyl phosphonate, tridecylphosphonate, triethylphosphonate, triheptylphosphonate, triisopropyl phosphonate, trimethylphosphonate, trioctadecyl phosphonate, trioctylphosphonate, tripentylphosphonate, triphenylphosphonate, tripropylphosphonate, trixylylphosphonate, or combinations thereof.

In an embodiment, the PPSC comprises a precursor to the organophosphorus compound. The organophosphorus compound precursor may comprise any material which may be converted to the organophosphorus compound which activates the PPSC under the conditions to which the hydrogenation catalyst is exposed and that is compatible with the other components of the PPSC. In an embodiment, the organophosphorus compound precursor can be represented by the general formula of $(R)_x(OR')_yP$; wherein x and y are integers ranging from 0 to 3 and x plus y equals 3; wherein each R may be hydrogen, a hydrocarbyl group, or combinations thereof; and wherein each R' may a hydrocarbyl group. The organophosphorus compound precursor may include without limitation phosphines, phosphites, phosphinites, phosphonites, or combinations thereof. In an embodiment, the organophosphorus compound precursor comprises a phosphine that can form a phosphine oxide when exposed to an oxidizing agent and/or temperatures greater than about 20° C. In an embodiment, the organophosphorus compound precursor comprises a phosphite that can form a phosphate when exposed to an oxidizing agent and/or temperatures greater than about 20° C. In an embodiment, the organophosphorus compound precursor comprises a phosphinite that can form a phosphinate when exposed to oxidizing agent and/or temperatures greater than about 20° C. In an embodiment, the organophosphorus compound precursor comprises a phosphonite that can form a phosphonate when exposed to air and/or temperatures greater than about 20° C.

In an embodiment, the organophosphorus compound comprises phosphines, which can be represented by the general formula of $(R)_3P$; wherein each R may be hydrogen, a hydrocarbyl group, or combinations thereof. Examples of phosphines suitable for use as phosphine oxide precursors in this disclosure include without limitation (1-methylethyl)diphenylphosphine, 2-ethylphenyldiphenyl phosphine, 4-(diphenylmethyl)phenyl]diphenylphosphine, bis(2-methylphenyl)(2-methylpropyl)phosphine, butyldiethylphosphine, butyldimethylphosphine, butyldiphenylphosphine, butyldipropylphosphine, crecyldiphenylphosphine, cyclohexyldiphenylphosphine, decyldiethylphosphine, decyldimethylphosphine, decyldiphenylphosphine, dibutyl(2-methylphenyl)phosphine, dicyclohexylphenylphosphine, diethyl(3-methylphenyl)phosphine, ethyldibutylphosphine, ethyldimethylphosphine, ethyldioctylphosphine, ethyldiphenylphosphine, ethyldipropylphosphine, heptyldibutylphosphine, heptyldiethylphosphine, heptyldimethyl phosphine, heptyldipentylphosphine, heptyldiphenylphosphine, hexyldibutylphosphine, hexyldiethylphosphine, hexyldimethyl phosphine, hexyldipentylphosphine, hexyldiphenylphosphine, methylbis(4-methylphenyl)phosphine, methyldibutylphosphine, methyldidecylphosphine, methyldiethylphosphine, methyldiphenylphosphine, methyldipropylphosphine, octyldimethylphosphine, octyldiphenylphosphine, pentyldibutylphosphine, pentyldiethylphosphine, pentyldimethylphosphine, pentyldiphenylphosphine, phenyldibutylphosphine, phenyldiethylphosphine, phenyldimethylphosphine, phenyldipropylphosphine, propyldibutylphosphine, propyldimethylphosphine, propyldiphenylphosphine, tri(2,3-dichloropropyl)phosphine, tri(2,6-dimethylphenyl)phosphine, tri(2-chloroethyl)phosphine, tri(nonylphenyl)phosphine, tris(2,6-dimethylphenyl)phosphine, tris(2-methylphenyl)phosphine, tris(4-methylphenyl)phosphine, tris(methoxyphenyl)phosphine, tris[4-(1,1-dimethylethyl)phenyl]phosphine, or combinations thereof. In some embodiments, the phosphines suitable for use in this disclosure include without limitation tributylphosphine, tricresyl phosphine, tricyclohexyl phosphine, tridecylphosphine, triethylphosphine, triheptylphosphine, triisopropylphosphine, trimethylphosphine, trioctadecyl phosphine, trioctylphosphine, tripentylphosphine, triphenylphosphine, tripropylphosphine, tri-t-butylphosphine, tritolylphosphine, trixylylphosphine, or combinations thereof.

In an embodiment, the organophosphorus compound comprises phosphites, which can be represented by the general formula of $(OR')_3P$; wherein each R' may a hydrocarbyl group. Examples of phosphites suitable for use as phosphate precursors in this disclosure include without limitation (1-methylethyl)diphenylphosphite, 2-ethylphenyldiphenyl phosphite, 4-(diphenylmethyl)phenyl]diphenylphosphite, bis(2-methylphenyl)(2-methylpropyl)phosphite, butyldiethylphosphite, butyldimethylphosphite, butyldiphenylphosphite, butyldipropylphosphite, crecyldiphenylphosphite, cyclohexyldiphenylphosphite, decyldiethylphosphite, decyldimethylphosphite, decyldiphenylphosphite, dibutyl(2-methylphenyl)phosphite, dicyclohexylphenylphosphite, diethyl(3-methylphenyl)phosphite, ethyldibutylphosphite, ethyldimethylphosphite, ethyldioctylphosphite, ethyldiphenylphosphite, ethyldipropylphosphite, heptyldibutylphosphite, heptyldiethylphosphite, heptyldimethyl phosphite, heptyldipentylphosphite, heptyldiphenylphosphite, hexyldibutylphosphite, hexyldiethylphosphite, hexyldimethyl phosphite, hexyldipentylphosphite, hexyldiphenylphosphite, methylbis(4-methylphenyl)phosphite, methyldibutylphosphite, methyldidecylphosphite, methyldiethylphosphite, methyldiphenylphosphite, methyldipropylphosphite, octyldimethylphosphite, octyldiphenylphosphite, pentyldibutylphosphite, pentyldiethylphosphite, pentyldimethylphosphite, pentyldiphenylphosphite, phenyldibutylphosphite, phenyldiethylphosphite, phenyldimethylphosphite, phenyldipropylphosphite, propyldibutylphosphite, propyldimethylphosphite, propyldiphenylphosphite, tri(2-chloroethyl)phosphite, tri(nonylphenyl)phosphite, tris(2,3-dichloropropyl)phosphite, tris(2,6-dimethylphenyl)phosphite, tris(2-methylphenyl)phosphite, tris(4-methylphenyl)phosphite, tris(methoxyphenyl)phosphite, tris[4-(1,1-dimethylethyl)phenyl]phosphite, tri-t-butylphosphite, or combinations thereof. In some embodiments, the phosphites suitable for use in this disclosure include without limitation tributylphosphite, tricresyl phosphite, tricyclohexyl phosphite, tridecylphosphite, triethylphosphite, triheptylphosphite, triisopropylphosphite, trimethylphosphite, trioctadecyl phosphite, trioctylphosphite, tripentylphosphite, triphenylphosphite, tripropylphosphite, tritolylphosphite, trixylylphosphite, or combinations thereof.

In an embodiment, the organophosphorus compound comprises phosphinites, which can be represented by the general formula of $(R)_2(OR')_1P$; wherein each R may be hydrogen, a hydrocarbyl group, or combinations thereof; and wherein each R' may a hydrocarbyl group. Examples of phosphinites suitable for use as phosphate precursors in this disclosure include without limitation (1-methylethyl)diphenylphosphinite, 2-ethylphenyldiphenyl phosphinite, 4-(diphenylmethyl)phenyl]diphenylphosphinite, bis(2-methylphenyl)(2-methylpropyl)phosphinite, butyldiethylphosphinite, butyldimethylphosphinite, butyldiphenylphosphinite, butyldipropylphosphinite, crecyldiphenylphosphinite, cyclohexyldiphenylphosphinite, decyldiethylphosphinite, decyldimethylphosphinite, decyldiphenylphosphinite, dibutyl(2-methylphenyl)phosphinite, dicyclohexylphenylphosphinite, diethyl(3-methylphenyl)phosphinite, ethyldibutylphosphinite, ethyldimethylphosphinite, ethyldioctylphosphinite, ethyldiphenylphosphinite, ethyldipropylphosphinite, heptyldibutylphosphinite, heptyldiethylphosphinite, heptyldimethyl phosphinite, heptyldipentylphosphinite, heptyldiphenylphosphinite, hexyldibutylphosphinite, hexyldiethylphosphinite, hexyldimethyl phosphinite, hexyldipentylphosphinite, hexyldiphenylphosphinite, methylbis(4-methylphenyl)phosphinite, methyldibutylphosphinite, methyldidecylphosphinite, methyldiethylphosphinite, methyldiphenylphosphinite, methyldipropylphosphinite, octyldimethylphosphinite, octyldiphenylphosphinite, pentyldibutylphosphinite, pentyldiethylphosphinite, pentyldimethylphosphinite, pentyldiphenylphosphinite, phenyldibutylphosphinite, phenyldiethylphosphinite, phenyldimethylphosphinite, phenyldipropylphosphinite, propyldibutylphosphinite, propyldimethylphosphinite, propyldiphenylphosphinite, tri(2-chloroethyl)phosphinite, tri(nonylphenyl)phosphinite, tris(2,3-dichloropropyl)phosphinite, tris(2,6-dimethylphenyl)phosphinite, tris(2-methylphenyl)phosphinite, tris(4-methylphenyl)phosphinite, tris(methoxyphenyl)phosphinite, tris[4-(1,1-dimethylethyl)phenyl]phosphinite, tri-t-butylphosphinite, or combinations thereof. In some embodiments, the phosphinites suitable for use in this disclosure include without limitation tributylphosphinite, tricresyl phosphinite, tricyclohexyl phosphinite, tridecylphosphinite, triethylphosphinite, triheptylphosphinite, triisopropylphosphinite, trimethylphosphinite, trioctadecyl phosphinite, trioctylphosphinite, tripentylphosphinite, triphenylphosphinite, tripropylphosphinite, tritolylphosphinite, trixylylphosphinite, or combinations thereof.

In an embodiment, the organophosphorus compound comprises phosphonites, which can be represented by the general formula of $(R)_1(OR')_2P$; wherein each R may be hydrogen, a hydrocarbyl group, or combinations thereof; and wherein each R' may a hydrocarbyl group. Examples of phosphonites suitable for use as phosphate precursors in this disclosure include without limitation (1-methylethyl)diphenylphosphonite, 2-ethylphenyldiphenyl phosphonite, 4-(diphenylmethyl)phenyl]diphenylphosphonite, bis(2-methylphenyl)(2-methylpropyl)phosphonite, butyldiethylphosphonite, butyldimethylphosphonite, butyldiphenylphosphonite, butyldipropylphosphonite, crecyldiphenylphosphonite, cyclohexyldiphenylphosphonite, decyldiethylphosphonite, decyldimethylphosphonite, decyldiphenylphosphonite, dibutyl(2-methylphenyl)phosphonite, dicyclohexylphenylphosphonite, diethyl(3-methylphenyl)phosphonite, ethyldibutylphosphonite, ethyldimethylphosphonite, ethyldioctylphosphonite, ethyldiphenylphosphonite, ethyldipropylphosphonite, heptyldibutylphosphonite, heptyldiethylphosphonite, heptyldimethyl phosphonite, heptyldipentylphosphonite, heptyldiphenylphosphonite, hexyldibutylphosphonite, hexyldiethylphosphonite, hexyldimethyl phosphonite, hexyldipentylphosphonite, hexyldiphenylphosphonite, methylbis(4-methylphenyl)phosphonite, methyldibutylphosphonite, methyldidecylphosphonite, methyldiethylphosphonite, methyldiphenylphosphonite, methyldipropylphosphonite, octyldimethylphosphonite, octyldiphenylphosphonite, pentyldibutylphosphonite, pentyldiethylphosphonite, pentyldimethylphosphonite, pentyldiphenylphosphonite, phenyldibutylphosphonite, phenyldiethylphosphonite, phenyldimethylphosphonite, phenyldipropylphosphonite, propyldibutylphosphonite, propyldimethylphosphonite, propyldiphenylphosphonite, tri(2-chloroethyl)phosphonite, tri(nonylphenyl)phosphonite, tris(2,3-dichloropropyl)phosphonite, tris(2,6-dimethylphenyl)phosphonite, tris(2-methylphenyl)phosphonite, tris(4-methylphenyl)phosphonite, tris(methoxyphenyl)phosphonite, tris[4-(1,1-dimethylethyl)phenyl]phosphonite, tri-t-butylphosphonite, or combinations thereof. In some embodiments, the phosphonites suitable for use in this disclosure include without limitation tributylphosphonite, tricresyl phosphonite, tricyclohexyl phosphonite, tridecylphosphonite, triethylphosphonite, triheptylphosphonite, triisopropylphosphonite, trimethylphosphonite, trioctadecyl phosphonite, trioctylphosphonite, tripentylphosphonite, triphenylphosphonite, tripropylphosphonite, tritolylphosphonite, trixylylphosphonite, or combinations thereof. In an embodiment, the organophosphorus compound and/or organophosphorus compound precursor may be present in the mixture for the preparation of the PPSC in an amount of from about 0.005 wt. % to about 5 wt. % based on the weight of phosphorus to the total weight of the PPSC, alternatively from about 0.01 wt. % to about 1 wt. %, alternatively from about 0.05 wt. % to about 0.5 wt. %. The amount of organophosphorus compound and/or phosphorus incorporated into the PPSC may be in the range described herein for the amount of organophosphorus compound and/or precursor used to prepare the PPSC.

In an embodiment, the PPSC may further comprise one or more selectivity enhancers. Suitable selectivity enhancers include, but are not limited to, Group 1B metals, Group 1B metal compounds, silver compounds, fluorine, fluoride compounds, sulfur, sulfur compounds, alkali metals, alkali metal compounds, alkaline metals, alkaline metal compounds, iodine, iodide compounds, or combinations thereof. In an embodiment, the PPSC comprises one or more selectivity enhancers which may be present in total in the mixture for preparation of the PPSC in an amount of from about 0.001 to about 10 wt. % based on the total weight of the PPSC, alternatively from about 0.01 to about 5 wt. %, alternatively from about 0.01 to about 2 wt. %. The amount of selectivity enhancer incorporated into the PPSC may be in the range described herein for the amount of selectivity enhancer used to prepare the PPSC.

In an embodiment, the selectivity enhancer comprises silver (Ag), silver compounds, or combinations thereof. Examples of suitable silver compounds include without limitation silver nitrate, silver acetate, silver bromide, silver chloride, silver iodide, silver fluoride, or combinations thereof. In an embodiment, the selectivity enhancer comprises silver nitrate. The PPSC may be prepared using silver nitrate in an amount of from about 0.005 wt. % to about 5 wt. % silver based on the total weight of the PPSC, alternatively from about 0.01 wt. % to about 1 wt. % silver, alternatively from about 0.05 wt. % to about 0.5 wt. %. The amount of silver incorporated into the PPSC may be in the range described herein for the amount of silver nitrate used to prepare the PPSC.

In an embodiment, the selectivity enhancer comprises alkali metals, alkali metal compounds, or combinations thereof. Examples of suitable alkali metal compounds include without limitation elemental alkali metal, alkali metal halides (e.g., alkali metal fluoride, alkali metal chloride, alkali metal bromide, alkali metal iodide), alkali metal oxides, alkali metal carbonate, alkali metal sulfate, alkali metal phosphate, alkali metal borate, or combinations thereof. In an embodiment, the selectivity enhancer comprises potassium fluoride (KF). In another embodiment, the PPSC is prepared using an alkali metal compound in an amount of from about 0.01 wt. % to about 5 wt. % based on the total weight of the PPSC, alternatively from about 0.05 wt. % to about 2 wt. %, alternatively from about 0.1 wt. % to about 1 wt. %. The amount of alkali metal incorporated into the PPSC may be in the range described herein for the amount of alkali metal compound used to prepare the PPSC.

In an embodiment, a method of preparing a PPSC may initiate with the contacting of an inorganic support with a palladium-containing compound to form a supported palladium composition. The contacting may be carried out using any suitable technique. For example, the inorganic support may be contacted with the palladium-containing compound by incipient wetness impregnation of the support with a palladium-containing solution. In such embodiments, the resulting supported palladium composition may have greater than about 90 wt %, alternatively from about 92 wt % to about 98 wt %, alternatively from about 94 wt % to about 96% of the palladium concentrated near the periphery of the palladium supported composition, as to form a palladium skin.

The palladium skin can be any thickness as long as such thickness can promote the hydrogenation processes disclosed herein. Generally, the thickness of the palladium skin can be in the range of from about 1 micron to about 3000 microns, alternatively from about 5 microns to about 2000 microns, alternatively from about 10 microns to about 1000 microns, alternatively from about 50 microns to about 500 microns. Examples of such methods are further described in more details in U.S. Pat. Nos. 4,404,124 and 4,484,015, each of which is incorporated by reference herein in its entirety.

Any suitable method may be used for determining the concentration of the palladium in the skin of the palladium supported composition and/or the thickness of the skin. For example, one method involves breaking open a representative sample of the palladium supported composition particles and treating the palladium supported composition particles with a dilute alcoholic solution of N,N-dimethyl-para-nitrosoaniline. The treating solution reacts with the palladium to give a red color that can be used to evaluate the distribution of the palladium. Yet another technique for measuring the concentration of the palladium in the skin of the palladium supported composition involves breaking open a representative sample of catalyst particles, followed by treating the particles with a reducing agent such as hydrogen to change the color of the skin and thereby evaluate the distribution of the palladium. Alternatively, the palladium skin thickness may be determined using the electron microprobe method.

The supported palladium composition formed by contacting the inorganic support with the palladium-containing solution optionally may be dried at a temperature of from about 15° C. to about 150° C., alternatively from about 30° C. to about 100° C., alternatively from about 60° C. to about 100° C.; and for a period of from about 0.1 hour to about 100 hours, alternatively from about 0.5 hour to about 20 hours, alternatively from about 1 hour to about 10 hours. Alternatively, the palladium supported composition may be calcined. This calcining step can be carried out at temperatures up to about 850° C., alternatively of from about 150° C. to about 700° C., alternatively from about 150° C. to about 600° C., alternatively from about 150° C. to about 500° C.; and for a period of from about 0.2 hour to about 20 hours, alternatively from about 0.5 hour to about 20 hours, alternatively from about 1 hour to about 10 hours.

In an embodiment, a method of preparing a PPSC further comprises contacting the supported palladium composition with an organophosphorus compound of the type described herein (e.g., phosphine oxide, phosphate, an organophosphorus compound precursor such as an phosphate or an phosphine). The contacting may be carried out in any suitable manner that will yield a selective hydrogenation catalyst meeting the parameters described herein such as for example by incipient wetness impregnation. Briefly, the organophosphorus compound may comprise phosphine oxide which is dissolved in a solvent, such as for example, water, acetone, isopropanol, etc., to form a phosphine oxide containing solution. The supported palladium composition may be added to the phosphine oxide containing solution to form a palladium/phosphine oxide supported composition (herein this particular embodiment of the PPSC is referred to as a Pd/PO composition).

In some embodiments, one or more selectivity enhancers of the type described previously herein may be added to the supported palladium composition prior to or following the contacting of same with an organophosphorus compound. In an embodiment, this addition can occur by soaking the supported palladium composition (with or without the organophosphorus compound) in a liquid comprising one or more suitable selectivity enhancers. In another embodiment, this addition can occur by incipient wetness impregnation of the supported palladium composition (with or without an organophosphorus compound) with liquid comprising one or more suitable selectivity enhancers to form an enhanced supported palladium composition.

In an embodiment, silver may be added to the supported palladium composition (without an organophosphorus compound). For example, the supported palladium composition can be placed in an aqueous silver nitrate solution of a quantity greater than that necessary to fill the pore volume of the composition. The resulting material is a palladium/silver supported composition (herein this particular embodiment of the PPSC is referred to as a Pd/Ag composition). In an embodiment, the Pd/Ag composition is further contacted with an organophosphorus compound. The contacting may be carried out as described above to form a palladium/silver/phosphine oxide composition. In another embodiment, the Pd/Ag composition is further contacted with a phosphine oxide compound (herein this particular embodiment of the PPSC is referred to as a Pd/Ag/PO composition).

In an embodiment, one or more alkali metals may be added to the Pd/Ag composition (prior to or following contacting with an organophosphorus compound) using any suitable technique such as those described previously herein. In an embodiment, the selectivity enhancer comprises potassium fluoride, and the resulting material is a palladium/silver/alkali metal fluoride supported composition (herein this particular embodiment of the PPSC is referred to as a Pd/Ag/KF composition).

In an embodiment, the supported palladium composition is contacted with both an alkali metal halide and a silver compound (prior to or following contacting with an organophosphorus compound). Contacting of the supported palladium composition with both an alkali metal halide and a silver compound may be carried out simultaneously; alternatively the contacting may be carried out sequentially in any user-desired order.

In an embodiment, one or more selectivity enhancers are contacted with the supported palladium composition prior to contacting the composition with an organophosphorus compound. In such embodiments, the resulting composition comprising Pd/Ag, Pd/KF, or Pd/Ag/KF may be calcined under the conditions described previously herein, and subsequently contacted with an organophosphorus compound. For example, phosphine oxide (PO) may be added to the Pd/Ag, Pd/KF, and/or Pd/Ag/KF compositions to provide Pd/Ag/PO, Pd/KF/PO, and/or Pd/Ag/KF/PO compositions. In an alternative embodiment, one or more selectivity enhancers are contacted with the supported palladium composition following contacting of the composition with an organophosphorus compound. For example, Ag and/or KF may be added to the Pd/PO composition to provide Pd/Ag/PO, Pd/KF/PO, and/or Pd/Ag/KF/PO compositions. In yet another alternative embodiment, one or more selectivity enhancers may be contacted with the palladium supported composition and an organophosphorus compound simultaneously.

In an embodiment, a PPSC formed in accordance with the methods disclosed herein comprises an α-alumina support, palladium, and an organophosphorus compound. In an alternative embodiment, a PPSC formed in accordance with the methods disclosed herein comprises an α-alumina support, palladium, an organophosphorus compound (e.g., phosphine oxide) and one or more selectivity enhancers, (e.g., silver and/or potassium fluoride). The PPSC (Pd/PO, Pd/Ag/PO, Pd/KF/PO, and/or the Pd/Ag/KF/PO compositions) can be dried to form a dried PPSC. In some embodiments, this drying step can be carried out at a temperature in the range of from about 0° C. to about 150° C., alternatively from about 30° C. to about 100° C., alternatively from about 50° C. to about 80° C.; and for a period of from about 0.1 hour to about 100 hours, alternatively from about 0.5 hour to about 20 hours, alternatively from about 1 hour to about 10 hours. In an embodiment, the organophosphorus compound comprises an organophosphorus compound precursor which upon exposure to air and/or the temperature ranges used during drying of the aforementioned composition is converted to an organophosphorus compound of the type described herein.

The dried PPSC may be reduced using hydrogen gas or a hydrogen gas containing feed, e.g., the feed stream of the selective hydrogenation process, thereby providing for optimum operation of the selective hydrogenation process. Such a gaseous hydrogen reduction may be carried out at a temperature in the range of from, for example, about 0° C. to about 150° C., alternatively 30° C. to about 100° C., alternatively about 50° C. to about 80° C.

In an embodiment, a method of preparing a PPSC comprises contacting an inorganic support with a palladium-containing compound (e.g., palladium chloride, palladium nitrate) to form a palladium supported composition; drying and calcining the palladium supported composition to form a dried and calcined palladium supported composition. The dried and calcined palladium supported composition may then be contacted with a silver-containing compound (e.g., silver nitrite, silver fluoride) to form a Pd/Ag composition which may then be dried and/or calcined to form a dried and/or calcined Pd/Ag composition. The dried and/or calcined Pd/Ag composition may be contacted with an alkali metal fluoride (e.g., potassium fluoride) to form a Pd/Ag/KF composition which is then dried and calcined. The dried and calcined Pd/Ag/KF composition may then be contacted with an organophosphorus compound (e.g., phosphine oxide or precursor) to form a PPSC. In an alternative embodiment, the Pd/Ag/KF composition may be added to an unsaturated hydrocarbon and the organophosphorus compound may be separately added to the unsaturated hydrocarbon so that the Pd/Ag/KF composition contacts the organophosphorus compound to form the PPSC while in contact with the unsaturated hydrocarbon. The PPSC may be further processed by drying the PPSC to form a dried PPSC. The contacting, drying, and calcining may be carried out using any suitable technique and conditions such as those described previously herein.

In an embodiment, the PPSC catalyses a selective hydrogenation process. In such processes the PPSC may be contacted with an unsaturated hydrocarbon stream primarily containing unsaturated hydrocarbons, e.g., ethylene, but also containing a highly unsaturated hydrocarbon, e.g., acetylene. The contacting may be executed in the presence of hydrogen at conditions effective to selectively hydrogenate the highly unsaturated hydrocarbon to an unsaturated hydrocarbon. In an embodiment, the PPSCs of the type disclosed herein are used in the hydrogenation of highly unsaturated hydrocarbons such as for example and without limitation acetylene, methylacetylene, propadiene, butadiene or combinations thereof.

Figure 1:
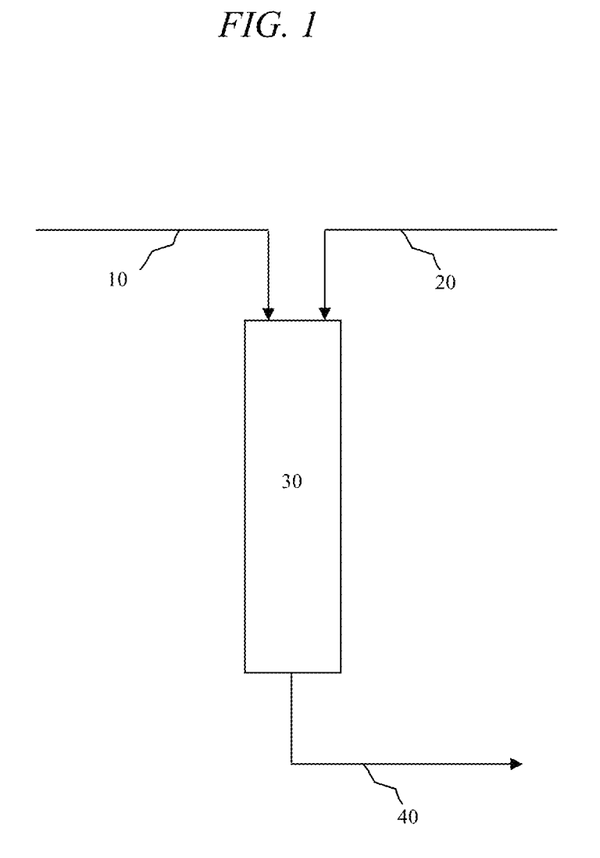
FIG. 1 depicts a process flow diagram of an embodiment of a selective hydrogenation process.
Figure 2:
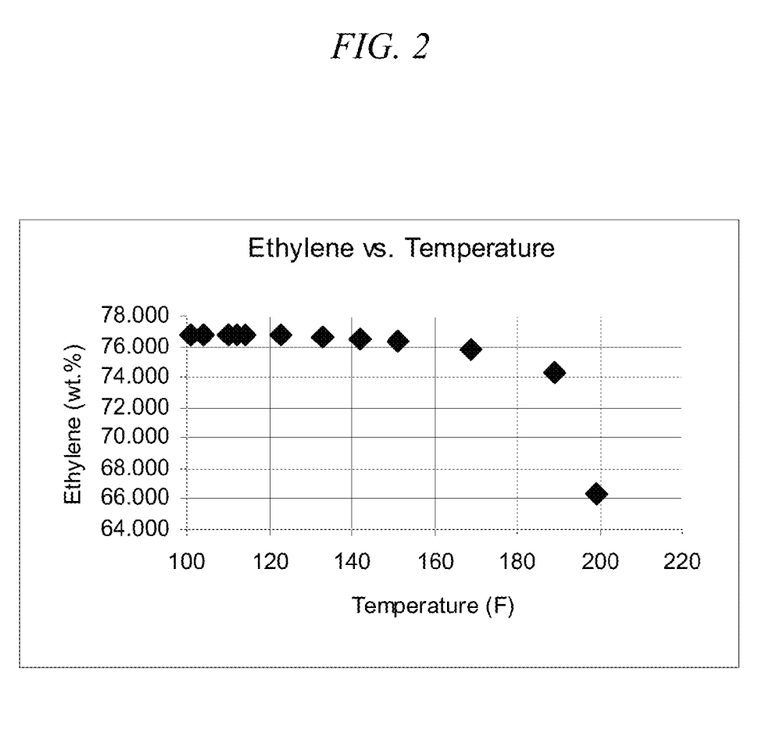
FIG. 2 is a plot of ethylene weight percentage in reactor effluent as a function of temperature for the sample from Example 1.

FIG. 1 illustrates an embodiment of a hydrogenation process that utilizes a PPSC of the type disclosed herein. The hydrogenation process includes feeding an unsaturated hydrocarbon stream 10 and a hydrogen ($H_2$) stream 20 to a hydrogenation reactor 30 within which the PPSC is disposed. The unsaturated hydrocarbon stream 10 primarily comprises one or more unsaturated hydrocarbons, but it may also contain one or more highly unsaturated hydrocarbons such as for example and without limitation acetylene, methylacetylene, propadiene, and butadiene. Alternatively, unsaturated hydrocarbon stream 10 and hydrogen stream 20 may be combined in a single stream that is fed to hydrogenation reactor 30.

In an embodiment, reactor 30 is a selective hydrogenation reactor that may belong to an acetylene removal unit of an unsaturated hydrocarbon production plant in a backend configuration. As used herein, "backend" refers to the location of the acetylene removal unit in an unsaturated hydrocarbon production unit that receives the lower boiling fraction from a deethanizer fractionation tower that receives the higher boiling fraction from a demethanizer fractionation tower which receives a feed from an unsaturated hydrocarbon production process.

In an embodiment, reactor 30 is a selective hydrogenation reactor that may belong to an acetylene removal unit of an unsaturated hydrocarbon production plant in a frontend deethanizer configuration. As used herein, "frontend deethanizer" refers to the location of the acetylene removal unit in an unsaturated hydrocarbon production unit that receives the lower boiling fraction from a deethanizer fractionation tower that receives a feed from an unsaturated hydrocarbon production process.

In an embodiment, reactor 30 is a selective hydrogenation reactor that may belong to an acetylene removal unit of an unsaturated hydrocarbon production plant in a frontend depropanizer configuration. As used herein, "frontend depropanizer" refers to the location of the acetylene removal unit in an unsaturated hydrocarbon production unit that receives the lower boiling fraction from a depropanizer fractionation tower that receives a feed from an unsaturated hydrocarbon production process.

In an embodiment, reactor 30 is a selective hydrogenation reactor that may belong to an acetylene removal unit of an unsaturated hydrocarbon production plant in a raw gas configuration. As used herein, "raw gas" refers to the location of the acetylene removal unit in an unsaturated hydrocarbon production unit that receives a feed from an unsaturated hydrocarbon production process without any intervening hydrocarbon fractionation.

It is understood that hydrogenation reactor 30, and likewise the selective hydrogenation catalysts disclosed herein, are not limited to use in backend acetylene removal units, frontend deethanizer units, frontend depropanizer, or raw gas units and may be used in any process wherein a highly unsaturated hydrocarbons contained within an unsaturated hydrocarbon stream is selectively hydrogenated to a unsaturated hydrocarbon.

In those embodiments wherein the acetylene removal unit is in a backend configuration, the highly unsaturated hydrocarbon being fed to the hydrogenation reactor 30 comprises acetylene. The mole ratio of the hydrogen to the acetylene being fed to hydrogenation reactor 30 may be in the range of from about 0.1 to about 10, alternatively from about 0.2 to about 5, alternatively from about 0.5 to about 3.

In those embodiments wherein the acetylene removal unit is in a front end deethanizer, front-end depropanizer or raw gas configuration, the highly unsaturated hydrocarbon being fed to the hydrogenation reactor 30 comprises acetylene. In such an embodiment, the mole ratio of the hydrogen to the acetylene being fed to the hydrogenation reactor 30 may be in the range of from about 10 to about 3000, alternatively from about 10 to about 2000, alternatively from about 10 to about 1500.

In those embodiments wherein the acetylene removal unit is in a front-end depropanizer or raw gas configuration, the highly unsaturated hydrocarbon being fed to the hydrogenation reactor 30 comprises methylacetylene. In such an embodiment, the mole ratio of the hydrogen to the methylacetylene being fed to the hydrogenation reactor 30 may be in the range of from about 3 to about 3000, alternatively from about 5 to about 2000, alternatively from about 10 to about 1500.

In those embodiments wherein the acetylene removal unit is in a front-end depropanizer or raw gas configuration, the highly unsaturated hydrocarbon being fed to the hydrogenation reactor 30 comprises propadiene. In such an embodiment, the mole ratio of the hydrogen to the propadiene being fed to the hydrogenation reactor 30 may be in the range of from about 3 to about 3000, alternatively from about 5 to about 2000, alternatively from about 10 to about 1500.

In another embodiment, reactor 30 may represent a plurality of reactors. The plurality of reactors may optionally be separated by a means to remove heat produced by the reaction. The plurality of reactors may optionally be separated by a means to control inlet and effluent flows from reactors or heat removal means allowing for individual or alternatively groups of reactors within the plurality of reactors to be regenerated. The selective hydrogenation catalyst may be arranged in any suitable configuration within hydrogenation reactor 30, such as a fixed catalyst bed.

Carbon monoxide may also be fed to reactor 30 via a separate stream (not shown), or it may be combined with hydrogen stream 20. In an embodiment, the amount of carbon monoxide being fed to reactor 30 during the hydrogenation process is less than about 0.15 mol % based on the total moles of fluid being fed to reactor 30.

Hydrogenation reactor 30 may be operated at conditions effective to selectively hydrogenate highly unsaturated hydrocarbons to one or more unsaturated hydrocarbons upon contacting the selective hydrogenation catalyst in the presence of the hydrogen. The conditions are desirably effective to maximize hydrogenation of highly unsaturated hydrocarbons to unsaturated hydrocarbons and to minimize hydrogenation of highly unsaturated hydrocarbons to saturated hydrocarbons. In some embodiments, acetylene may be selectively hydrogenated to ethylene. Alternatively methylacetylene may be selectively hydrogenated to propylene; alternatively propadiene may be selectively hydrogenated to propylene. Alternatively butadiene may be selectively hydrogenated to butenes. In some embodiments, the temperature within the hydrogenation zone may be in the range of from about 5° C. to about 300° C., alternatively from about 10° C. to about 250° C., alternatively from about 15° C. to about 200° C. In some embodiments, the pressure within the hydrogenation zone may be in the range of from about 15 (204 kPa) to about 2,000 (13,890 kPa) pounds per square inch gauge (psig), alternatively from about 50 psig (446 kPa) to about 1,500 psig (10,443 kPa), alternatively from about 100 psig (790 kPa) to about 1,000 psig (6,996 kPa).

Referring back to FIG. 1, an effluent stream 40 comprising unsaturated hydrocarbons, including the one or more monoolefins produced in hydrogenation reactor 30, and any unconverted reactants exit hydrogenation reactor 30. In an embodiment, effluent stream 40 primarily comprises ethylene comprises less than about 5 ppm, alternatively less than about 1 ppm of highly unsaturated hydrocarbons.

In an embodiment, a PPSC of the type describe herein may have a comparable catalytic activity when compared to an otherwise similar catalyst lacking an organophosphorus compound. The comparable catalytic activity may translate to a comparable clean up temperature. Herein, the clean up temperature is referred to as T1 and refers to the temperature at which the acetylene concentration drops below 20 ppm in a feed stream comprising unsaturated hydrocarbon and highly unsaturated hydrocarbons such as acetylenes and diolefins. In an embodiment, a PPSC of the type disclosed herein may have a T1 of from about 80° F. to about 160° F., alternatively from about 85° F. to about 140° F., alternatively from about 90° F. to about 120° F.

In an embodiment, a PPSC may exhibit an increased selectivity when compared to an otherwise similar catalyst lacking an organophosphorus compound of the type described herein. Herein selectivity refers to a comparison between the rate at which the catalyst converts a highly unsaturated hydrocarbon to an unsaturated hydrocarbon, herein termed Conversion 1, and the rate at which the catalyst converts an unsaturated hydrocarbon to a saturated hydrocarbon, herein termed Conversion 2. A PPSC may display an increased rate of Conversion 1 and a decreased rate of Conversion 2 when compared to an otherwise similar catalyst prepared in the absence of an organophosphorus compound of the type described herein. Conversion 2 is highly exothermic and can lead to runaway reactions or the uncontrollable conversion of unsaturated hydrocarbons to saturated hydrocarbons. The higher selectivity of the PPSC may result in a reduction in the incidence of runaway reactions and increase the operating window of the hydrogenation process.

An operating window ($\Delta T$) is defined as the difference between a runaway temperature (T2) at which 3 wt % of ethylene is hydrogenated from a feedstock comprising highly unsaturated and unsaturated hydrocarbons, and the clean up temperature (T1). $\Delta T$ is a convenient measure of the catalyst selectivity and operation stability in the hydrogenation of highly unsaturated hydrocarbons (e.g., acetylene) to unsaturated hydrocarbons (e.g., ethylene). The more selective a catalyst, the higher the temperature beyond T1 required to hydrogenate a given unsaturated hydrocarbons (e.g., ethylene). The T2 is coincident with the temperature at which a high probability of runway ethylene hydrogenation reaction could exist in an adiabatic reactor. Therefore, a larger $\Delta T$ translates to a more selective catalyst and a wider operation window for the complete acetylene hydrogenation.

In an embodiment, a PPSC of the type disclosed herein may have an operating window of from about 35° F. to about 120° F., alternatively from about 40° F. to about 80° F., alternatively from about 45° F. to about 60° F. The operating window of a PPSC of the type described herein may be increased by greater than about 10%, alternatively greater than about 15%, alternatively greater than about 20% when compared to an otherwise similar catalyst prepared in the absence of an organophosphorus compound.

In an embodiment, a PPSC of the type described herein when used as a hydrogenation catalyst produces a reduced amount of heavies. As used herein, heavies refer to molecules having four or more carbon atoms per molecule. Selective hydrogenation catalysts can produce heavies by oligomerizing the highly unsaturated hydrocarbons (e.g., acetylenes and diolefins) that are present in the feed stream. The presence of heavies is one of a number of contributors to the fouling of the selective hydrogenation catalysts that result in catalyst deactivation. The deactivation of the selective hydrogenation catalyst results in the catalyst having a lower activity and selectivity to unsaturated hydrocarbons. In an embodiment, a PPSC of the type described herein exhibits a reduction in the weight percent of wt % C4+ produced at T1 of from about 1 wt. % to about 25 wt. % alternatively from about 1.5 wt. % to about 20 wt. % alternatively from about 2 wt. % to about 15 wt. %.

In an embodiment, a PPSC comprises an organophosphorus compound having a low boiling point as described previously herein. Herein, the organophosphorus compound having a low boiling point is referred to as an LBP organophosphorus compound. In such embodiments, the PPSC may display activity comparable to or greater than an otherwise similar catalyst prepared in the absence of an organophosphorus compound. In an embodiment, a hydrogenation catalyst comprising a palladium supported catalyst composition with an LBP organophosphorus compound of the type described herein may result in the catalyst displaying a selectivity and activity comparable to that of a hydrogenation catalyst comprising one or more selectivity enhancers (e.g., Pd/Ag, Pd/KF, or Pd/Ag/KF). In another embodiment, treatment of a hydrogenation catalyst comprising a single selectivity enhancer (e.g., Pd/Ag or Pd/KF) with an LBP organophosphorus compound of the type described herein may result in the catalyst displaying a selectivity and activity comparable to that of a hydrogenation catalyst comprising at least two selectivity enhancers (e.g., Pd/Ag/KF).

A method for the selective hydrogenation of a hydrocarbon feed comprising highly unsaturated and unsaturated hydrocarbons may comprise the preparation of a PPSC catalyst comprising a LBP organophosphorus compound and contacting of the PPSC with the hydrocarbon feed in a reactor having an initial temperature (T0). The LBP organophosphorus compound may remain associated with the PPSC upon start of the reaction at T0, however, over time and as the temperature increases above the boiling point of the LBP organophosphorus compound, the LBP organophosphorus compound may be evaporated (i.e., boiled off) from the PPSC. The PPSC comprising the LBP organophosphorus compound may display an increased activity over some time period and enhanced initial selectivity wherein the LBP organophosphorus compound is associated with the PPSC. This may be advantageous for reactions employing a fresh catalyst as the LBP organophosphorus compound may allow for a more stable operation and a reduction in the potential for a runaway reaction due to the increase in catalyst selectivity and predictable catalytic activity as the composition stabilizes. Following the loss of the LBP organophosphorus compound, the resulting composition may display an activity and selectivity comparable to that of an otherwise similar catalyst prepared in the absence of an organophosphorus compound.

In an alternative embodiment, a method for the selective hydrogenation of a hydrocarbon feed comprising highly unsaturated and unsaturated hydrocarbons comprises the preparation of a PPSC comprising a high boiling point organophosphorus compound of the type described previously herein and contacting of the PPSC with the hydrocarbon feed. The high boiling point organophosphorus compound may remain associated with the PPSC throughout the lifetime of the catalyst providing the reaction temperature remains below the boiling point of the high boiling point organophosphorus compound. The PPSC comprising the high boiling point organophosphorus compound may display improvements in characteristics such as catalytic activity and selectivity when compared to an otherwise similar catalyst composition prepared in the absence of an organophosphorus compound.

EXAMPLES

The disclosure having been generally described, the following examples are given as particular embodiments of the disclosure and to demonstrate the practice and advantages thereof. It is understood that the examples are given by way of illustration and are not intended to limit the specification of the claims to follow in any manner.

In the following examples, the performance of various PPSCs was compared to similar catalysts lacking an organophosphorus compound. Each catalyst contained palladium (Pd) and an alumina support. Additional catalyst details are found in each example. The catalyst was evaluated by placing 20 ml of catalyst sample inside a stainless steel reactor with 0.65 inches inside diameter. A thermowell of 3/16 inches diameter was inserted through the catalyst bed. The reactor temperature was regulated by circulating a heating medium, which contained a mixture of ethylene glycol and water, over the exterior surface of the reactor. The catalyst was first reduced at about 100° F. to 200° F. for about 1 to 2 hours under hydrogen gas flowing at 200 ml/min at 200 pounds per square inch gauge (psig). There, a hydrocarbon containing fluid, typically a feed from the top of a deethanizer or depropanizer fractionation tower in an ethylene plant, containing hydrogen, methane, ethane, ethylene, acetylene, and carbon monoxide was continuously introduced to the reactor at a flow rate of 900 mL per minute at 200 psig. The reactor temperature was increased until the hydrogenation reaction ran away, i.e., the uncontrollable hydrogenation of ethylene was allowed to occur. During the runaway, the heat of hydrogenation built up such that the reactor temperature exceeded about 250° F. The reactor was then allowed to cool to room temperature before data collection was started.

Feed (900 mL/min at 200 psig) was passed over the catalyst continuously while holding the temperature constant before sampling the exit stream by gas chromatography. The catalyst temperature was determined by inserting a thermocouple into the thermowell and varying its position until the highest temperature was observed. The temperature of the heating medium was then raised a few degrees, and the testing cycle was repeated until 3 weight % of ethylene was hydrogenated. The cleanup temperature, T1, and the operating window, ΔT were determined as described previously. All temperatures are in degrees Fahrenheit. Further, the selectivity to heavies was calculated on a weight basis using the following equation, where "heavies" refer to hydrocarbons having four or more carbon atoms:

selectivity to heavies=(weight of heavies made/weight of acetylene consumed)*100

Example 1

The ability of various catalyst compositions to hydrogenate a deethanizer feed stream was investigated. A first control catalyst sample, Catalyst A1, was prepared on α-$Al_2O_3$ pellets supplied by Süd Chemie of Louisville, Ky., USA in the form of 4 mm×4 mm tablets as described in U.S. Pat. No. 4,484,015 which is incorporated by reference herein in its entirety. The α-$Al_2O_3$ pellets had a surface area of about 5 to about 7 $m^2/g$ (determined by the BET method employing $N_2$). Catalyst A1 contained 230 ppm by weight (ppmw) palladium and 920 ppmw silver. Catalyst A1 was evaluated for selective hydrogenation of acetylene using a feed whose compositions is presented in Table 1 Catalyst A1 was determined to have a T1 of 97° F., ΔT of 49° F., and C4+ make at T1 of 19.5%.

TABLE 1

| Reactor Feed Component | Mol % |
|---|---|
| Hydrogen | 26.63 |
| Methane | 25.81 |
| Acetylene | 0.1613 |
| Ethylene | 47.36 |
| Carbon monoxide | 0.0338 |

A second control sample, Catalyst A2 was prepared as follows: 0.220 g KF was dissolved in water ($H_2O$) to form a 16.22 g solution which was used to impregnate 50.06 g of Catalyst A1. Catalyst A2 was then dried at 90° C. for 1 hour, at 200° C. for 1 hour, at 300° C. for 1 hour, and at 400° C. for 3 hours resulting in a catalyst comprising 0.3 wt. % KF. The performance of Catalyst A2 was then tested in a selective hydrogenation process using a feed described in Table 1. T1, T2, and ΔT were determined and the results are tabulated in Table 2. Additionally, Catalyst A2 was found to have a C4+ make at T1 of 15.2%.

TABLE 2

| T1 (° F.) | 110 |
|---|---|
| T2 (° F.) | 174 |
| ΔT (° F.) | 64 |

Catalyst A3 was prepared as follows: 0.190 g triphenyl phosphine oxide (TPPO) was dissolved in acetone to form a 15.08 g solution which was used to impregnate 50.53 g of Catalyst A1. Catalyst A3 was then air dried and purged overnight with a vacuum and contained 0.044 wt. % of phosphorus. The Catalyst A3 was then used to selectively hydrogenate a hydrocarbon feed the components of which are presented in Table 1. T1, T2, and ΔT were determined and the results are tabulated in Table 3. Additionally, Catalyst A3 has a C4+ make at T1 of 12.8%. Catalyst A3 prepared using a phosphine oxide (i.e., TPPO) has a slightly broader operation window than either of the control samples (Catalysts A1 or A2), further Catalyst A3 produced a reduced amount of heavies at T1 than either control sample.

TABLE 3

| T1 (° F.) | 102 |
|---|---|
| T2 (° F.) | 167 |
| ΔT (° F.) | 65 |

Catalyst A4 was prepared as follows: 0.099 g of TPPO was dissolved in isopropanol to form a 7.5 g solution which was used to impregnate 25.35 g Catalyst A2. Catalyst A4 was then air dried and placed in an oven at 100° C. for 3 hours. Catalyst A4 contained 0.044 wt. % of phosphorus. The performance of Catalyst A4 was tested in a selective hydrogenation process with a feed given in Table 1. T1, T2, and ΔT were determined and the results are tabulated in Table 4. Additionally, Catalyst A4 has a C4+ make at T1 of 12.4%, which shows how much fouling agents are produced at T1. Catalyst A4 displayed a broader operation window than either of the control catalyst samples prepared in the absence of an organophosphorus compound and a reduced production of heavies.

TABLE 4

| T1 (° F.) | 113 |
|---|---|
| T2 (° F.) | 193 |
| ΔT (° F.) | 80 |

Catalyst A5 was prepared as follows: 0.383 g TPPO was dissolved in isopropanol to form a 16.86 g solution which was used to impregnate 50.40 g of Catalyst A1. Catalyst A5 was air dried and then dried for 4 hours in an oven at 100° C. Catalyst A5 contained 0.088 wt. % of phosphorus. The performance of Catalyst A5 was tested in a selective hydrogenation process. The reactor feed components are shown in Table 1. T1, T2, and ΔT were determined and the results are tabulated in Table 5. Additionally, Catalyst A5 has a C4+ make at T1 of 7.4%. Catalyst A5 displayed a broader operation window than either of the control catalyst samples prepared in the absence of an organophosphorus compound and a reduced production of heavies.

TABLE 5

| T1 (° F.) | 108 |
|---|---|
| T2 (° F.) | 183 |
| ΔT (° F.) | 75 |

Catalyst A6 was prepared as follows: 0.052 g triethyl phosphine oxide (TEPO) was dissolved in acetone to form a 18.5 g solution which was used to impregnate 50.47 g of Catalyst A2. Catalyst A6 was then air dried and purged overnight with a vacuum. The TEPO content in Catalyst A6 was determined by ion coupled plasma (ICP) to be 253 ppmw (i.e., 0.025 wt. %) of phosphorus. The performance of Catalyst A6 was tested in a selective hydrogenation process. The reactor feed components are tabulated in Table 1. T1, T2, and ΔT for ethylene and ethane were determined and the results are tabulated in Table 6. Additionally, Catalyst A6 has a C4+ make at T1 of 25%. Catalyst A6 displayed a broader operation window than either of the control catalyst samples prepared in the absence of an organophosphorus compound (i.e., TEPO) but displayed a higher production of heavies which may be attributable to a variety of factors including for example analytical error.

TABLE 6

| | |
|---|---|
| T1 (° F.) | 109 |
| T2 (° F.) | 188 |
| ΔT (° F.) | 79 |

Catalyst A7 was prepared as follows: 0.081 g TEPO was dissolved in acetone to form a 15.33 g solution which was used to impregnate 50.63 g of Catalyst A1. Catalyst A7 was then air dried and purged overnight with a vacuum. Catalyst A7 contained 0.044 wt. % of phosphorus. The performance of Catalyst A7 was tested in a selective hydrogenation process. The reactor feed components are shown in Table 1. T1 and ΔT were determined and the results are tabulated in Table 7. Additionally, Catalyst A7 has a C4+ make at T1 of 17% and spent Catalyst A7 was determined to contain 356 ppmw phosphorus by ICP. Catalyst A7 displayed a broader operation window than either of the control catalyst samples prepared in the absence of an organophosphorus compound.

TABLE 7

| | |
|---|---|
| T1 (° F.) | 99 |
| T2 (° F.) | 161 |
| ΔT (° F.) | 62 |

A comparison of catalyst components and performance in a deethanizer C2 feed is shown in Table 8. Referring to Table 8, collectively, the results demonstrated that the addition of organophosphorus compound (e.g., phosphine oxide) to a Pd/Ag or Pd/Ag/KF hydrogenation catalyst increased the operation window of the catalyst as was shown by comparing Catalyst A1 vs. A3 and A5, as well as Catalyst A2 vs. A4 and A6.

Example 2

Catalyst A8 was prepared from the same support as Catalyst A1 from Example 1. Catalyst A8 contained 230 ppmw palladium and had no silver. The performance of Catalyst A8 was tested in a selective hydrogenation process. The reactor feed components are shown in Table 1. T1, T2, and ΔT were determined and the results are tabulated in Table 9. Additionally, Catalyst A8 has a C4+ make at T1 of 31.6%.

TABLE 9

| | |
|---|---|
| T1 (° F.) | 98 |
| T2 (° F.) | 131 |
| ΔT (° F.) | 33 |

Catalyst A9 was prepared as follows: 0.381 g TPPO was dissolved in isopropanol to form a 16.31 g solution which was used to impregnate 50.56 g of Catalyst A8. Catalyst A9 was air dried then dried in an oven at 100° C. for 3 hours and found to contain 0.088 wt. % of phosphorus. The performance of Catalyst A9 was tested in a selective hydrogenation process. The reactor feed components are shown in Table 1. T1, T2, and ΔT were determined and the results are tabulated in Table 10. Additionally, Catalyst A9 has a C4+ make at T1 of 23.7%. The results demonstrate the presence of an organophosphorus compound (i.e., TPPO) broadened the catalyst window when compared to Catalyst A8.

TABLE 10

| | |
|---|---|
| T1 (° F.) | 96 |
| T2 (° F.) | 136 |
| ΔT (° F.) | 40 |

Catalyst A10 was prepared as follows: 0.164 g of 85% concentrated phosphoric acid was diluted with deionized water (DI H$_2$O) to form a 15 g solution which was used to impregnate 50.36 g of Catalyst A1. Catalyst A10 was air dried and then dried in an oven at 150° C. for 3 hours. Catalyst A10 contained 0.08 wt. % of phosphorus. The performance of Catalyst A10 was tested in a selective hydrogenation process. The reactor feed components are shown in Table 1. T1, T2, and ΔT were determined and the results are tabulated in Table 11. Additionally, Catalyst A10 has a C4+ make at T1 of 21.3%. The results demonstrate the presence of phosphoric acid was ineffective when compared to an organic phosphine oxide (e.g., TPPO).

TABLE 8

| Catalyst | Palladium (ppmw) | Silver (ppmw) | Potassium (wt. %) | Phosphorus (wt. %) | Organo Phosphorus compound | Tclean-up (° F.) | Operation Window (° F.) | C4+ make at Tclean-up (%) |
|---|---|---|---|---|---|---|---|---|
| A1 | 230 | 920 | 0 | 0 | 0 | 97 | 49 | 19.5 |
| A2 | 230 | 920 | 0.3 | 0 | 0 | 110 | 64 | 15.2 |
| A3 | 230 | 920 | 0 | 0.044 | TPPO | 102 | 65 | 12.8 |
| A4 | 230 | 920 | 0.3 | 0.044 | TPPO | 113 | 80 | 12.4 |
| A5 | 230 | 920 | 0 | 0.088 | TPPO | 108 | 75 | 7.4 |
| A6 | 230 | 920 | 0.3 | 0.025 | TEPO | 109 | 79 | 25 |

TABLE 11

| T1 (° F.) | 91 |
|---|---|
| T2 (° F.) | 131 |
| ΔT (° F.) | 40 |

A comparison for the components and performance of Catalysts A7-A10 is shown in Table 12. Referring to Table 12, collectively the results demonstrated that the addition of an organic phosphine oxide to a catalyst increased the operation window of such catalyst as shown by comparing Catalyst A8 vs. A9, A7, vs. A10.

TABLE 12

| Catalyst | Palladium (ppmw) | Silver (ppmw) | Potassium (wt. %) | Phosphorus (wt. %) | Organo Phosphorus compound | T clean-up (° F.) | Operation Window (° F.) | C4+ make at Tclean-up (%) |
|---|---|---|---|---|---|---|---|---|
| A7 | 230 | 920 | 0 | 0.044 | TEPO | 99 | 62 | 17.0% |
| A8 | 230 | 0 | 0 | 0 | 0 | 98 | 33 | 31.6 |
| A9 | 230 | 0 | 0 | 0.044 | TPPO | 96 | 40 | 23.7 |
| A10 | 230 | 920 | 0 | 0.08 | Phosphoric acid | 91 | 40 | 21.3 |

Example 3

The performance of various catalysts was tested on a feed from a depropanizer. Catalyst B1 (control) was prepared on α-Al$_2$O$_3$ pellets supplied by Süd Chemie of Louisville, Ky., USA in the form of 4 mm×4 mm tablets as described in U.S. Pat. No. 4,484,015. The α-Al$_2$O$_3$ pellets had a surface area of about 5 to about 7 m$^2$/g (determined by the BET method employing N$_2$). Catalyst B1 contained 400 ppmw palladium and 400 ppmw silver. The performance of Catalyst B1 was tested in a selective hydrogenation process. The reactor feed components are shown in Table 13.

TABLE 13

| Reactor Feed | |
|---|---|
| Component | mol % |
| Hydrogen | 21.98 |
| Methane | 45.13 |
| Acetylene | 0.2340 |
| Ethylene | 26.09 |
| Methylacetylene | 0.0702 |
| Propadiene | 0.0780 |
| Propylene | 6.40 |
| Carbon monoxide | 0.0233 |

T1, T2, and ΔT were determined and the results are tabulated in Table 14. Additionally, Catalyst B1 has a C4+ make at T1 of 31.4%.

TABLE 14

| T1 (° F.) | 98 |
|---|---|
| T2 (° F.) | 140 |
| ΔT (° F.) | 42 |

Catalyst B2 was prepared from Catalyst B1 by addition of 0.1 wt. % potassium using potassium fluoride. The performance of Catalyst B2 was tested in a selective hydrogenation process. The reactor feed components are shown in Table 13. T1, T2, and ΔT were determined and the results are tabulated in Table 15. Additionally, Catalyst B2 has a C4+ make at T1 of 20.2%. Catalyst B2 displayed a broader operating window than Catalyst B1.

TABLE 15

| T1 (° F.) | 102 |
|---|---|
| T2 (° F.) | 153 |
| ΔT (° F.) | 51 |

Catalyst B3 was prepared as follows: 1.534 g TPPO was dissolved with 60.1 g isopropanol to form a solution which was used to impregnate 200.3 g of Catalyst B1. Catalyst B3 contained 0.088 wt. % of phosphorus. The performance of Catalyst B3 was tested in a selective hydrogenation process using a feed shown in Table 13. T1, T2, and ΔT were determined and the results are tabulated in Table 16. Additionally, Catalyst B3 has a C4+ make at T1 of 6.0%. Catalyst B3 displayed a broader operation window and a reduced formation of heavies than either of the control catalyst samples prepared in the absence of an organophosphorus compound (i.e., TPPO).

TABLE 16

| T1 (° F.) | 102 |
|---|---|
| T2 (° F.) | 171 |
| ΔT (° F.) | 69 |

Catalyst B4 was prepared as follows: 1.541 g of TPPO was dissolved in isopropanol to form a solution which was used to impregnate 200.3 g of Catalyst B2. Catalyst B4 was then air dried and placed overnight in an oven at 80° C. Catalyst B4 contained 0.088 wt. % of phosphorus. The performance of Catalyst B4 was tested in a selective hydrogenation process using the feed shown in Table 13. T1, T2, and ΔT were determined and the results are tabulated in Table 17. Additionally, Catalyst B4 has a C4+ make at T1 of 14.9%. Catalyst B3 displayed a broader operation window and a reduced formation of heavies than either of the control catalyst samples prepared in the absence of an organophosphorus compound (i.e., TPPO). Catalyst B4 also displayed a broader processing window than Catalyst B3. Without wishing to be limited by theory, the broader operation window displayed by Catalyst B4 may be attributable to the synergy effect between the amounts of palladium, silver, phosphorus, and the organophosphorus compound with the alkali metal.

TABLE 17

| T1 (° F.) | 104 |
|---|---|
| T2 (° F.) | 218 |
| ΔT (° F.) | 114 |

A comparison of the components and performance of Catalysts B1-B4 in a depropanizer for C3 feed is shown in Table 18. The results demonstrated that the addition of organophosphorus compound to a catalyst increased the operation window of such catalyst as shown by comparing Catalyst B1 vs. B3 and Catalyst B2 vs. B4.

TABLE 18

| Catalyst | Palladium (ppmw) | Silver (ppmw) | Potassium (wt. %) | Phosphorus (wt. %) | Organo Phosphorus compound | Tclean-up (° F.) | Operation Window (° F.) | C4+ make at Tclean-up (%) |
|---|---|---|---|---|---|---|---|---|
| B1 | 400 | 400 | | | | 98 | 42 | 31.4 |
| B2 | 400 | 400 | 0.1 | | | 102 | 51 | 20.2 |
| B3 | 400 | 400 | | 0.088 | TPPO | 102 | 69 | 6.0 |
| B4 | 400 | 400 | 0.1 | 0.088 | TPPO | 104 | 114 | 14.9 |

While embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the embodiments of the present invention. The disclosures of all patents, patent applications, and publications cited herein are hereby incorporated by reference, to the extent that they provide exemplary, procedural or other details supplementary to those set forth herein.

What is claimed is:

1. A method of making a selective hydrogenation catalyst comprising:
   contacting a support with a palladium-containing compound to form a palladium supported composition;
   contacting the palladium supported composition with an organophosphorus compound to form a catalyst precursor; and
   reducing the catalyst precursor to form the catalyst.

2. The method of claim 1 wherein the organophosphorus compound is represented by the general formula $(R)_x(OR')_yP=O$, wherein x and y are integers ranging from 0 to 3 and x+y=3, wherein each R may be hydrogen, a hydrocarbyl group, or combinations thereof; and wherein each R' may a hydrocarbyl group.

3. The method of claim 1 wherein the organophosphorus compound comprises a phosphine oxide, phosphinate, phosphonate, phosphate, or combinations thereof.

4. The method of claim 1 wherein the organophosphorus compound is a product of an organophosphorus compound precursor represented by the general formula of $(R)_x(OR')_yP$, wherein x and y are integers ranging from 0 to 3 and x+y=3, wherein each R may be hydrogen, a hydrocarbyl group, or combinations thereof; and wherein each R' may a hydrocarbyl group.

5. The method of claim 4 wherein the organophosphorus compound precursor comprises a phosphite, a phosphonite, a phosphinite, a phosphine, an organic phosphine, or combinations thereof.

6. The method of claim 1 wherein the organophosphorus compound has a boiling point of greater than about 300° C.

7. The method of claim 1 wherein:
   the palladium-containing compound is present in an amount of from about 0.005 wt. % to about 5 wt. % based on the total weight of the catalyst; and
   the organophosphorus compound is present in an amount of from about 0.005 wt. % to about 5 wt. % based on the total weight of the catalyst.

8. The method of claim 1 further comprising contacting the catalyst precursor with a selectivity enhancer.

9. The method of claim 8 wherein the selectivity enhancer is present in an amount of from about 0.005 wt. % to about 5 wt. % based on the total weight of the catalyst.

10. The method of claim 1 further comprising contacting the palladium supported composition with Group 1B metals, Group 1B metal compounds, silver compounds, fluorine, fluoride compounds, sulfur, sulfur compounds, alkali metal, alkali metal compounds, alkaline metals, alkaline metal compounds, iodine, iodide compounds, or combinations thereof.

11. The method of claim 1 further comprising contacting the palladium supported composition with elemental silver, silver nitrate, silver acetate, silver bromide, silver chloride, silver iodide, silver fluoride, or combinations thereof.

12. The method of claim 1 further comprising contacting the palladium supported composition with an alkali metal compound.

13. The method of claim 12 wherein the alkali metal compound comprises elemental alkali metal, alkali metal fluoride, alkali metal chloride, alkali metal bromide, alkali metal iodide, alkali metal oxide, alkali metal carbonate, alkali metal sulfate, alkali metal phosphate, alkali metal borate, potassium fluoride, or combinations thereof.

14. The method of claim 12 wherein the alkali metal compound is present in an amount of from about 0.01 wt. % to about 5 wt. % based on the total weight of the catalyst.

15. The method of claim 1 further comprising drying the catalyst precursor at a temperature of from about 0° C. to about 150° C. for a time period of from about 0.1 hour to about 100 hours.

* * * * *